United States Patent
Whitall et al.

(10) Patent No.: US 8,845,494 B2
(45) Date of Patent: Sep. 30, 2014

(54) STEP TRAINER FOR ENHANCED PERFORMANCE USING RHYTHMIC CUES

(75) Inventors: Jill Whitall, Annapolis, MD (US); Sandra A. McCombe-Waller, Ellicott City, MD (US); Muniswamappa Anjanappa, Ellicott City, MD (US)

(73) Assignees: University of Maryland, Baltimore, Baltimore, MD (US); University of Maryland, Baltimore County, Baltimore, MD (US)

( * ) Notice: Subject to any disclaimer, the term of this patent is extended or adjusted under 35 U.S.C. 154(b) by 620 days.

(21) Appl. No.: 13/121,701

(22) PCT Filed: Sep. 29, 2009

(86) PCT No.: PCT/US2009/058713
§ 371 (c)(1),
(2), (4) Date: Mar. 30, 2011

(87) PCT Pub. No.: WO2010/039674
PCT Pub. Date: Apr. 8, 2010

(65) Prior Publication Data
US 2011/0184225 A1 Jul. 28, 2011

Related U.S. Application Data

(60) Provisional application No. 61/136,759, filed on Oct. 1, 2008.

(51) Int. Cl.
*A63B 22/00* (2006.01)
*A61B 5/103* (2006.01)
*A63B 69/00* (2006.01)
*A63B 24/00* (2006.01)
*A63B 71/06* (2006.01)
*A61H 3/00* (2006.01)

(52) U.S. Cl.
CPC ......... *A63B 71/0686* (2013.01); *A63B 2220/20* (2013.01); *A63B 2024/0068* (2013.01); *A63B 2225/50* (2013.01); *A63B 2071/0652* (2013.01); *A61H 3/00* (2013.01); *A63B 69/0028* (2013.01); *A63B 2220/40* (2013.01); *A63B 2220/802* (2013.01); *A63B 69/0035* (2013.01); *A63B 24/0003* (2013.01); *A63B 2220/22* (2013.01); *A63B 2220/44* (2013.01); *A63B 2071/063* (2013.01)
USPC ................................. 482/8; 482/54; 600/595

(58) Field of Classification Search
USPC .......................... 482/1–8, 51–54; 600/28, 595
See application file for complete search history.

(56) References Cited

U.S. PATENT DOCUMENTS 5,137,501 A * 8/1992 Mertesdorf .................... 482/57
5,919,149 A 7/1999 Allum (Continued)

FOREIGN PATENT DOCUMENTS

JP 2008-161228 7/2008

OTHER PUBLICATIONS

International Search Report and Written Opinion of International Application No. PCT/US2009/058713 dated May 12, 2010.

*Primary Examiner* — Stephen Crow
(74) *Attorney, Agent, or Firm* — Squire Patton Boggs (US) LLP

(57) ABSTRACT

A person's step length and rate may be measured, for example, through sensors that collect spatial and temporal gait parameter data. The measurements are then used to determine the rate of a rhythmic auditory cue to improve the person's gait. For example, a system links sensors to detect step rate and length to an audio cue provided to headphones, while providing the appropriate algorithms to accomplish real time adjustments to the audio cues as needed to better help change the person's step length vs. step rate ratio in a desired direction depending on therapeutic or performance goals.

20 Claims, 12 Drawing Sheets

(56) References Cited

U.S. PATENT DOCUMENTS

| | | | |
|---|---|---|---|
| 6,645,126 B1 | 11/2003 | Martin et al. | |
| 6,997,852 B2 * | 2/2006 | Watterson et al. | 482/1 |
| 7,628,730 B1 * | 12/2009 | Watterson et al. | 482/8 |
| 7,789,800 B1 * | 9/2010 | Watterson et al. | 482/8 |
| 7,985,164 B2 * | 7/2011 | Ashby | 482/8 |
| 8,269,826 B2 * | 9/2012 | Nieminen et al. | 348/77 |
| 8,303,500 B2 * | 11/2012 | Raheman | 600/301 |
| 2003/0139254 A1 * | 7/2003 | Chang | 482/1 |
| 2008/0234113 A1 | 9/2008 | Einav | |
| 2011/0071003 A1 * | 3/2011 | Watterson et al. | 482/8 |
| 2012/0323346 A1 * | 12/2012 | Ashby et al. | 700/91 |

* cited by examiner

Audio Cue Training Method 100

Audio Cuing Gait Improvement Device 200

Walking Surface

610: Typical acceleration profile of heel of each foot

Dynamic Audio Cuing Method 700

Audio Cuing
Gait Improvement Device
900

Audio Cuing Gait Improvement Method 1000

Chart 1100

STEP TRAINER FOR ENHANCED PERFORMANCE USING RHYTHMIC CUES

GOVERNMENT FUNDING

This invention was made with Government support under grant number AG030349, awarded by the National Institute of Health (NIH). The Government has certain rights in this invention.

FIELD OF THE INVENTION

Embodiments of the present invention relate to training an individual to change attributes of a gait, specifically the step length and step rate ratio for a given velocity, in response to an rhythmic auditory cue and, thereby, actively make changes to increase the spatial and temporal parameters of gait and increase speed.

BACKGROUND OF THE INVENTION

Recovery from a physiological or neurological injury is often difficult. Conventional physical rehabilitation following the injury focuses on restoring and/or building physical strength to resume pre-injury activities. For example, a patient may strengthen limbs through physical training, such as walking on a treadmill. However, various injuries may limit a patient's coordination and motor control, and these types of secondary conditions, although possibly improved through building physical strength, may continue to linger despite conventional therapies. For example, a stroke patient may develop asymmetrical control and coordination in the limbs, resulting in a limp or other gait abnormality. Specifically, they may alter their step length/rate ratio at a given speed to on that is inefficient for the purpose of improving gait speed.

This has applications for large number of individuals with disabling conditions. For example, persons suffering from peripheral neuropathy may experience numbness and tingling in their hands and feet, and these symptoms may cause ambulation impairment, such as trouble climbing stairs or maintaining balance. Gait abnormality is also common in persons with nervous system affections such as Stroke, Acquired Brain Injury, Multiple sclerosis, Parkinson's disease, Alzheimer's disease, Huntington's disease, amyotrophic lateral sclerosis (ALS), stroke (for example by, ischemia and/or reperfusion and blunt trauma), aging, traumatic brain injury, and Myasthenia gravis. Orthopedic corrective treatments may also manifest into gait abnormality, such as, for example, following a fracture or an arthroplasty (joint replacement).

Gait abnormality may persist even after physical conditions leading to the gait abnormality are resolved. For example, difficulty in walking due to arthritis or joint pains, resulting in an antalgic gait, may persist even after the pain is abated through treatment and medication. In particular, patients may develop improper gait habits that may persist, even if the primary condition is resolved or improved, due to the lost or impairment of proper gait form. Furthermore, conventional therapeutic techniques for gait abnormalities, such as having the patient move at a forced pace on a treadmill, may produce temporary improvements such as normalizing the gait between the patient's two legs, but these benefits are usually temporary, and do not carry over to over ground walking.

The persistent coordination and motor control limitations that impact gait may significantly limit the patient's ability to exist independently and to interact within the community. For example, the patient generally needs to be able to move at a sufficient pace to cross streets within a safe time period. Moreover, unnatural movement patterns may place undue physical stress on the patient's body, thereby leading to further injury that may lead to further gait limitations.

SUMMARY OF THE INVENTION

In response to these and other needs, embodiments of the present invention relate to the independent manipulation of two gait parameters that will change the step length/rate ratio at a given velocity comprising the use of audio cues. In addition, rhythmic auditory cueing may be used as a transition between treadmill physical rehabilitation and community living.

Embodiments of the present application relate to measuring a person's step length and rate, such as through sensors that collect gait parameter data. The measurements are used to determine the rate of a rhythmic auditory cue to improve the person's gait. For example, an embodiment of the present invention relates to a system that links sensors (for step length and step rate) to an audio cue provided to headphones, while providing the appropriate algorithms to accomplish real time adjustments to better help change the person's step length/rate ratio in a desired direction depending on therapeutic or performance goals.

In one embodiment, the present invention relates to a method that includes determining attributes of the ideal spatial and temporal gait parameters of a user. The actual gait parameters of the user are measured. An audio cue is produced based upon the ideal gait parameters and the actual gait parameters.

In another embodiment, an apparatus includes a processor configured to receive data from a sensor configured to measure attributes of a gait of a user. The processor is further configured to determine the rate of a audio cue using the received sensor data and attributes of the user that include the age, stature, and gender of the user and a desired gait change for that user.

Another embodiment of the present invention relates to a computer program embodied on a computer-readable medium, comprising computer-executable components. The components implement a method that includes determining attributes of ideal gait parameters for a user. The actual gait parameters of the user are measured. An audio cue is produced based upon the ideal gait parameters and the actual gait parameters.

BRIEF DESCRIPTION OF THE DRAWINGS

So that the manner in which the above recited embodiments of the invention are attained and can be understood in detail, a more particular description of the invention, briefly summarized above, may be obtained by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 5:
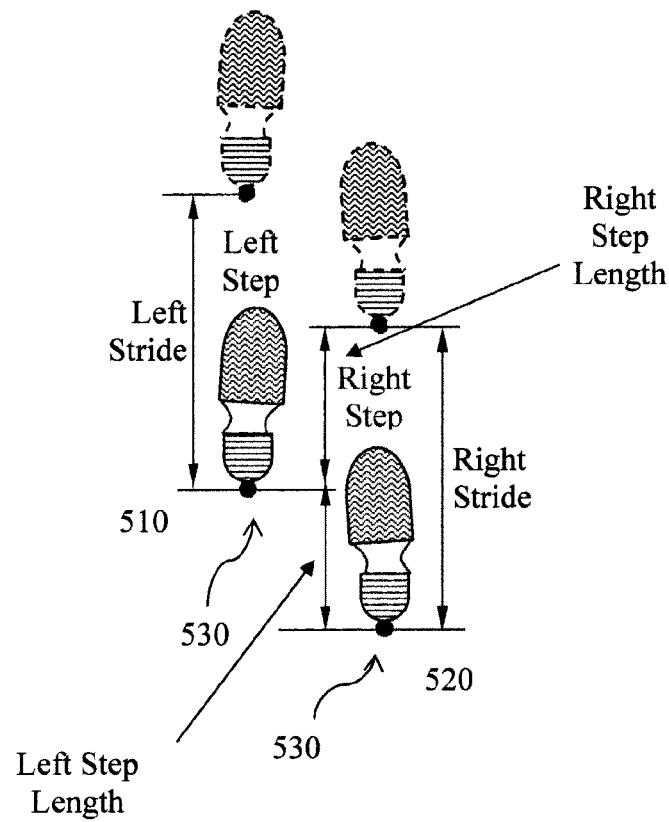
FIGS. 5 and 6A-6B depict aspects of gait attribute measurement in accordance with an embodiment of the present application.

Referring to FIG. 5, a schematic depiction 500 of a gait parameters includes a left foot 510 and right foot 520, each with a sensor 530. The expression "step length" is defined as a distance between the point of initial contact of one foot and the point of initial contact of the opposite foot. In a normal gait, right and left step lengths are the same, thereby having a step length symmetry of 1. The expression of a "step length" is defined to be the distance between successive points of initial contact of the same foot. Again, the right and left step lengths are equal for normal gait, with a step length symmetry of 1. The expression of "step rate" is defined to be the number of steps per minute. For example, a pedometer counts the number of steps and determines the distance by simply multiplying this number with keyed-in average step length. As described above, the gait sensors disclosed in various embodiments of the present invention, count the number of steps and measure the step length of each leg in real time.

Figure 1:
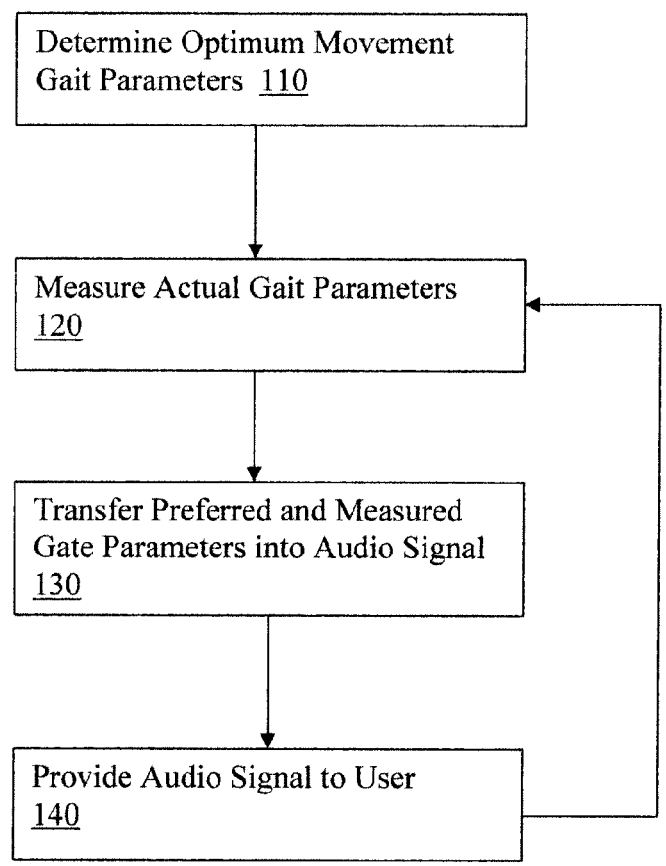
FIG. 1 depicts an audio cuing gait improvement method in accordance with an embodiment of the present application.

Embodiments of the present invention relate to addressing gait abnormalities or changing gait parameters, including, for example, increasing or decreasing stride length, step length, stride frequency, and step frequency. Referring to FIG. 1, for example, embodiments of the present application relate to a training method 100 for enhancing athletic performance and therapeutic outcomes or rehabilitation following a disease, condition, or occurrence affecting gait, using audio cues. In method 100, an optimum movement gait parameters are determined in step 110, and the actual gait parameters for a patient may be measured in step 120. The preferred gait parameters are transferred into an audio message in step 130, where the message includes audio cues designed to change the gait parameters. This audio message is then presented to the user in step 140 during physical activity such as walking, running, and jogging. These steps are described in greater detail below.

The determining of the gait parameters in step 110 may be accomplished in a variety of ways. As described in greater detail below, a gait cycle includes several factors related to the user's spatial and temporal parameters of movement, namely step length and step rate. For example, ideal gait parameters may be determined using the user's physical characteristics, such as the user's age, sex, height, weight, etc. Alternatively, ideal gait parameters can be defined in view of other healthy individuals with similar physical characteristics. The defined gait may be uniform for the patient's right and left sides, or may differ on each side according to the patient's specific needs.

In step 110, the measuring of the actual gait may include determining a stance and swing phase of the gait cycle. Similarly, the measuring of the actual spatial and temporal gait parameters may include measuring horizontal acceleration and angular acceleration. The measuring of actual spatial and temporal gait parameters may include using angular acceleration to calculate pitch angle. This measuring of the actual spatial and temporal gait parameters may include using angular acceleration to calculate step length.

The actual gait parameters may be measured in step 120 using various techniques. For example, a patient's gait can be observed and measured to determine various characteristics related to the patient's movement, including step length and step rate. Alternatively, a patient exercising on a treadmill presumably moves at a predefined velocity.

As described below, certain embodiments of the present invention have particular application with subjects who may had or are suffering from a disease or condition affecting gait selected from the group consisting of multiple sclerosis, Parkinson's disease, Alzheimer's disease, Huntington's disease, amyotrophic lateral sclerosis (ALS), stroke, aging, traumatic brain injury, and Myasthenia gravis. Alternatively, the subject may have undergone an orthopedic corrective treatment or be seeking to increase athletic performance.

Continuing with FIG. 1, an audio signal is formed in step 130 to cue the user of changes to the actual gait to better achieve the ideal gait. For example, as described in greater detail below, an audio cue indicating the desired gait timing and step length at a given velocity may be defined. In this way, a user may receive an indication of when to, and how far, to step. In other embodiments, also described below, the audio cue defined in step 130 may optionally provide feedback regarding differences between the ideal gait parameters defined in step 110 and the actual gait parameters measured in step 120. For example, a moderate tone audio cue may be provided to indicate that a step conforms in timing and length to the ideal gait parameters, and either a lower or higher audio cue may be provided to indicate when the actual step measured in step 120 too long or too short respectively compared to the ideal gait defined in 110.

In step 130, the rhythmic audio cue rate for a particular individual is determined by an assessment of the present step length/step rate ratio for that individual at a given velocity along with an assessment about what the preferred step length/step rate ratio should be for that individual. The assessment is made based on a therapist or coach's knowledge and judgment with reference to normative data for that individual based on age, gender and stature.

For example, if an individual had a natural step rate of 50 steps per minute and a step length of 0.33 meters and the judgment was that the step rate should be increased but the step length remain the same then a method of increasing the step rate would be to set the audio cue at a rate of, say 60 steps per minute and have the individual match this. The problem with this scenario is that the individual would likely also increase her step length due to natural instincts. In certain embodiments of the present invention, the step length is kept constant. For example, the constant step rate can be achieved on the treadmill by increasing the audio cue rate such that the step length remained constant at a given speed increase. Alternatively, as described below, with a patient moving over ground, a device could provide the 60 steps per minute cue rate and let the individual adjust to this and, at the same time, cue the individual to keep a constant step-length by using different tones to indicate shortening (or lengthening) the step-length. If the same individual were assessed to need the step length to be increased but the step rate remain the same then our method of increasing the step length would be, on the treadmill, to increase the treadmill speed while keeping the audio cue constant. In this way, as long as they keep to the beat, the individual would automatically increase their step-length while keeping their step-rate constant. Over ground, the same goal will be accomplished by keep the audio cue constant and changing the tone to indicate that the individual should increase their step length.

In the present application, the phrase "step rate" refers to the time between steps expressed as the number of steps per minute. Each footfall equals a step, so a left step is the time between a right footfall and subsequent left footfall and a right footfall is the time between a left footfall and subsequent right footfall.

In the present application, the "step length" is the distance between steps expressed as the average step footfall over a given time period. Each footfall equals a step, so a left step is the distance between a right footfall and subsequent left footfall and a right footfall is the distance between a left footfall and subsequent right footfall.

The rate of the audio signal determined in step 130 may be provided to the user in step 140. For example, the audio signal may by provided to a speaker or headphone to reproduce and present the audio cue to the user. It should be appreciated that although the present application refers to an audio cue, the signal formed in step 130 may be presented in alternative ways, such as through a visual or touch-based indication. In this way, the embodiments disclosed in the present application may be adapted for use by hearing-impaired users or in circumstances where an audio cue would not be heard, such as in noisy environments.

Optionally, as described below, the rhythmic audio cue is provided in step 140 to the user on a device simulating ambulation. The device simulating ambulation, such as a treadmill may include a moving belt configured to cause the subject to move at a specified speeds. Alternatively, as described below, in step 140, the rhythmic audio cue may be provided to the subject by a portable device. In this implementation, the rhythmic audio cue optionally includes signals having a beat and a tone, such that the signals are provided by the portable device at a beat to increase pace of the subject.

Figure 2:
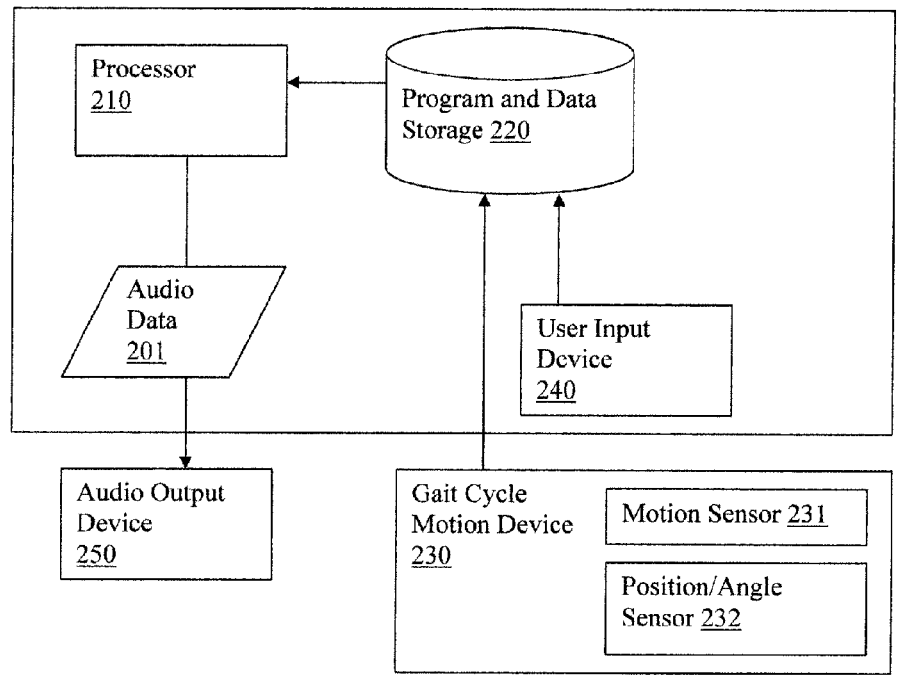
FIG. 2 depicts an audio cuing gait improvement device in accordance with an embodiment of the present application.

Referring now to FIG. 2, an audio cue gait improvement device 200 is described. The device 200 includes a processor 210 for forming audio cuing data 201. The processor 210 is connected to a program and data storage device 220 for acquiring the information and program instructions needed to form the audio cuing data 201. For example, the storage device 220 may be a hard drive or a writable memory for encoding stored data related to a user and that user's gait parameters and program instructions for forming the audio cuing data 201 using this stored data. The storage device 220 may receive data from a gait parameter sensor 230 that measures aspects of a person's movements. For example, the gait parameter sensor 230 may include a motion sensor 231 and a position sensor 232 that detect the relative motion and position of the user's feet or other lower extremities to determine the user's gait parameters. For example, the motion sensor, such as an accelerometer, may detect the amount and timing of relative changes in instantaneous motion, such as when the patient starts and stops each movement of a lower limb (i.e., foot steps). Similarly, the position sensor 232, such as a gyroscope, may detect relative changes in a position and angle of the lower extremity. The sensor 230 may be used on one or both lower limbs of the patient, depending on the patient's needs. The specific operations of the sensors 230 is described in greater detail below.

Alternatively, the user's gait parameters can be observed and the parameters manually entered through a user input device 240, such as a computer keyboard. Likewise, additional information related to the user and/or the gait parameters can also be manually provided to the storage device 220.

Using the audio data 201, an audio output device 250 may present the audio cuing to the patient at appropriate times. For example, the audio output device 250 may be a speaker or headphone to produce and present the audio cue to the user. As described above, the audio cue data may also be presented to the user as a visual or touch indication, according to the needs of the patient. The audio output device 250 provides the audio signal that will cue the individual as to how to alter their step length/step rate ratio by keeping time to the beat and, if over ground, by adjusting step length according to the tone pitch. Specifically, the processor 210 receives the measured step length and step rate of the individual at a given velocity and use these data along with the proposed changes of step length and step rate for a given velocity to provide data needed for the desired operation the audio output device 250.

Embodiments of the present invention relate to addressing gait abnormalities by treadmill training (TT) and rhythmic auditory cueing (RAC). As described below, TT generally encourages a patient to move at a defined pace and often has an immediate effect of producing a symmetrical gait, but these gains are often not maintained to produce immediate or long-term improvement because the patient tends to not maintain the symmetrical gait when off the treadmill. RAC, in which a rhythmic audio pattern is provided to the patient, often has immediate and/or long-term benefits for symmetry, for example, in stroke and Parkinson's patients. As described below, certain embodiments of the present invention relate to manipulating RAC and treadmill speed independently, thereby uniquely altering specific aspects of the gait parameters such as step length or step rate, depending on the preferred therapeutic target. This goal-directed training method cannot be accomplished by either TT alone or use of a simple metronome as a cue for over ground or community walking. Thus, embodiments of the present invention include enhancing step length (rather than step rate) for increasing walking speed, for example, by increasing the treadmill speed but keeping the RAC at a constant frequency (or vice versa.). Also, using this invention during over ground walking with modulating rhythmic audio cuing training may provide a mechanism in which the benefits of treadmill training can be translated to over ground walking (i.e., away from a treadmill or other exercise machine). This device optimizes both the treadmill training and the translational aspects of this gait training because patients can receive the rhythmic auditory cues without distraction and may also optionally receive continuous feedback about their leg movements to determine if and when resetting of the rhythmic auditory cueing is necessary.

Figure 3:
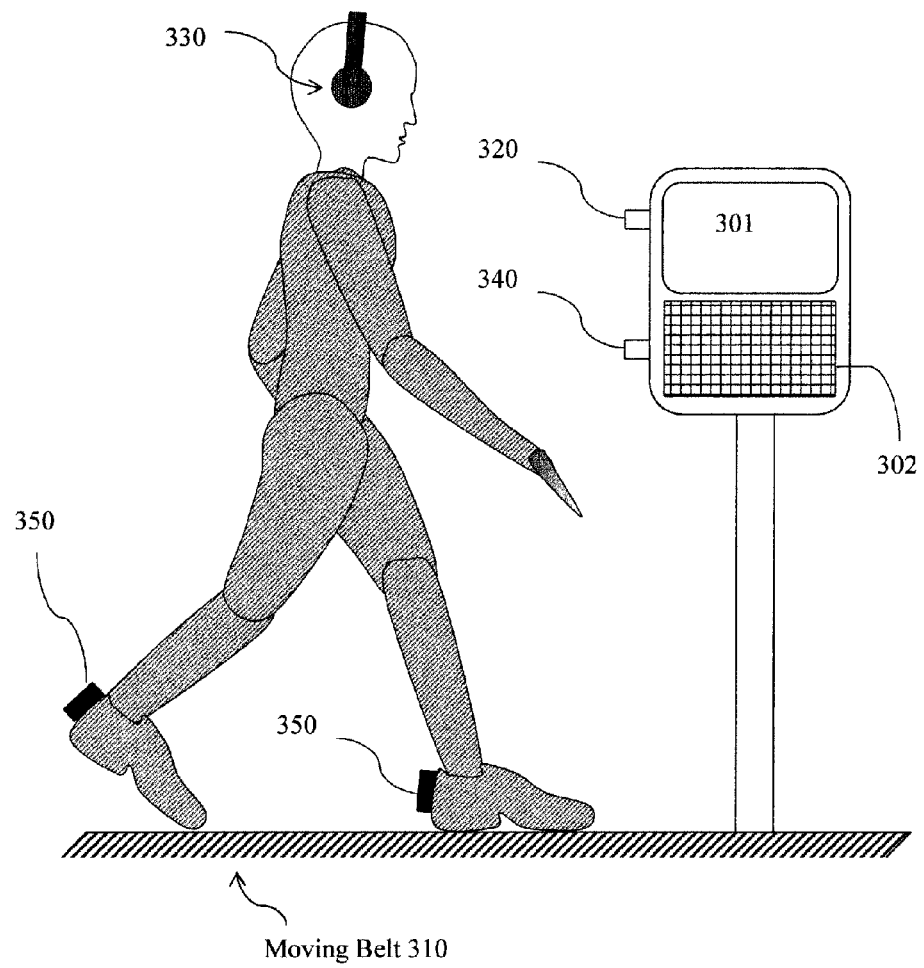
FIG. 3 depicts a supplied propulsion audio cuing gait improvement device in accordance with an embodiment of the present application.

Referring now to FIG. 3, an audio cue gait improvement system 300 for use with a treadmill is described. Similar to the device 200 described above, the system 300 includes a processor and a storage device (neither depicted) for forming audio cuing data. The system 300 may include a user interface that has, for example, a display 301 and an input device 302. A moving belt 310 driven by motor (also not depicted) travels at one or more preset speed(s), causing the user to move at that speed(s). The speed(s) of the moving belt 10 may be combined with other gait data to form the audio cuing data provided to the user. The audio cuing data may be sent by an audio data interface 320, such as a radio or a wireless data transmitter, to an audio output device 330, such as a headphone. Alternatively, the components in system 300 may be connected by wires for transmission of relevant data signals and commands. In addition to the speed information from the moving belt, the system 300 may receive gait data from other sources. For example, the system 300 may also include a gait data interface 340, such as a radio or a wireless data receiver, to receive data from a sensor 350. As described above, the sensor 350 may indicate the changes in the linear motion and/or angle of the foot.

It should be appreciated that although the sensors 350 are depicted as being affixed to the user's feet, the sensors may also be attached to the user at other locations as well, and gait data from these other locations may be incorporated within the scope of the present invention. For example, a sensor positioned near the user's knee may be used to determine the motion of the limb, and to compare the gait motions at the two knees. Similarly, useful gait data may be acquired from a sensor at the user's pelvis to compare pelvic symmetry during gait. Likewise, sensors at other locations on the user, such as the arms, may be used to better evaluate and promote the upper body's contribution to reciprocal gait.

Figure 4:
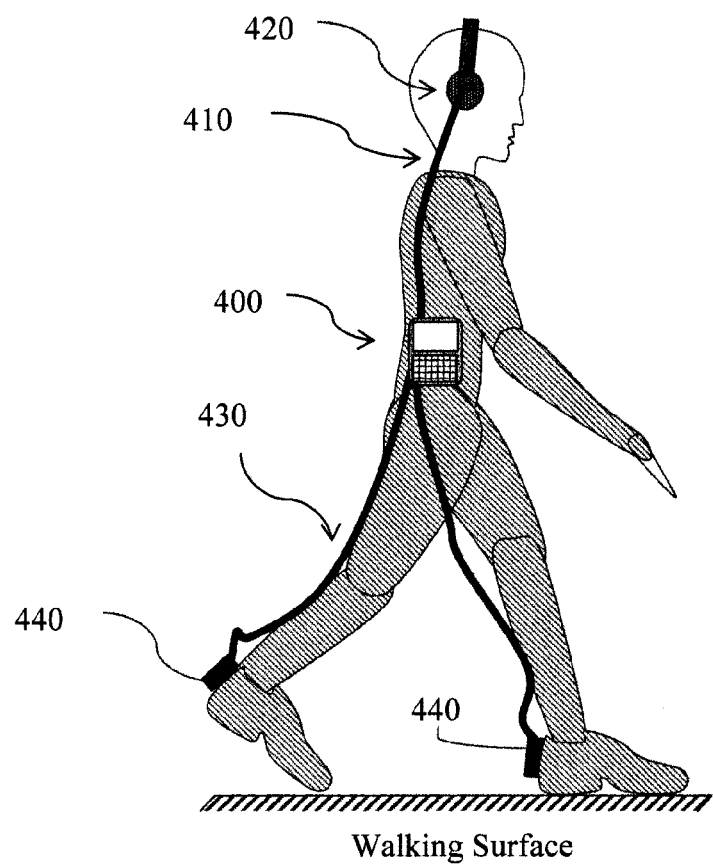
FIG. 4 depicts a portable audio cuing gait improvement device in accordance with an embodiment of the present application.

In another embodiment of the present invention depicted in FIG. 4, a portable device 400 may receive spatial and temporal gait parameter data and produce corresponding audio cuing. As described in greater detail below, the portable device 400 may be used to provide a comprehensive platform to implement both the treadmill training and the over ground walking rehabilitation for patients. The device 400 may measure gait parameters characteristics, such as step length and step rate in real-time and generate appropriate audio cues in accordance with conventional rehabilitation algorithms.

The portable device 400, as depicted in FIG. 4, is mounted preferably on the user's waist and is equipped with computation algorithms and a circuit to generate the desired rhythmic audio cue signals, as described above. The portable device 400 is connected by a first connection 410 to a headphone 420 to generate the rhythmic audio cues to both ears. Likewise, the portable device 400 is connected by a second connection 430 to one or more sensors 440 that may be mounted on the user's feet to monitor the user's gait parameters. First and second connections 410 and 430 may be wired connections for transmitting the relevant data and control signals. Alternatively, first and second connections 410 and 430 may include wireless communications, such as radio signals between the portable device 400 and headphone 420 and/or the sensors 440.

In this configuration, the portable device 400 may measure the step length and step rate in real-time and compute to generate a rhythmic auditory cue for playing over the headphones using built-in algorithms. Similarly, as described below, the portable device 400 may have additional capability to determine other parameters such as a step length/rate ratios, stance-swing ratio, step velocity etc. Optionally, the portable device 400 may include a data input device to adjust functions manually during training. Similarly, the portable device 400 optionally communicates with a personal computer (PC) for downloading data and updates in the algorithms.

Referring again to FIG. 5, sensors 530 for measuring step rate, step and step lengths may be based, for example, on global positioning systems (GPS), inertial sensors, and ultrasonic sensors. A GPS-based method tracks the location of the sensor(s) by satellite, and thereafter deduces the gait-related motion. The sensor 530 may also use a force sensor in the sole of the shoe to detect movements. Alternatively, as described in greater detail below and in FIGS. 6A-6B and 7, an inertia-based sensor may use an accelerometer and/or a gyroscope to measure acceleration and motion rates which can then be manipulated to calculate the desired step rate and lengths in real time for a given velocity. Alternatively, an ultrasonic-based sensors may use reflected ultrasonic sound signals to measure stride and step lengths, as depicted in FIG. 8.

In one embodiment of the present invention, the gait sensors 530 are inertial sensors that include an accelerometer for measuring acceleration and gravity induced reaction forces. A 3-axis accelerometer, such as a micro electro-mechanical systems (MEMs) model, may be used to detect magnitude and direction of the acceleration as a vector quantity to sense inclination, vibration, and shock. The sensor 530 may further include a gyroscope for measuring orientation of the foot during the gait cycle.

An inertial sensor 530 mounted on shoe near the Achilles tendon can give the acceleration of the foot with respect to the three dimensions. As described above, the step rate of the gait cycle corresponds to the number of steps per minute. The number of steps in a user's gait can be calculated from the vertical acceleration signal provided by the accelerometer sensor. For example, FIG. 6B depicts a typical vertical acceleration signal 610 representing one full step. The two spikes in the acceleration signal 610 represent that heel hitting the ground and the portion of the signal 610 between the peak represents the acceleration of the heel sensor 530 during the gait cycle. In this way, the number of steps in the gait cycle can be determined by adding the number of acceleration spikes in the acceleration signal 610 from the two sensors 530. For a normal gait (i.e., when symmetry=1 such that gait parameters for each foot are substantially equivalent), the number of total steps can be obtained by doubling the number of spikes from any one foot. If the person goes through the motion of walking but without any advancement in distance, the accelerometer in the sensor 530 still reports a spike in the output for each step. A processor in the gait improvement device 300, 400 may then decide whether the step is being counted towards advancement according to an encoded algorithm.

Figure 6A:
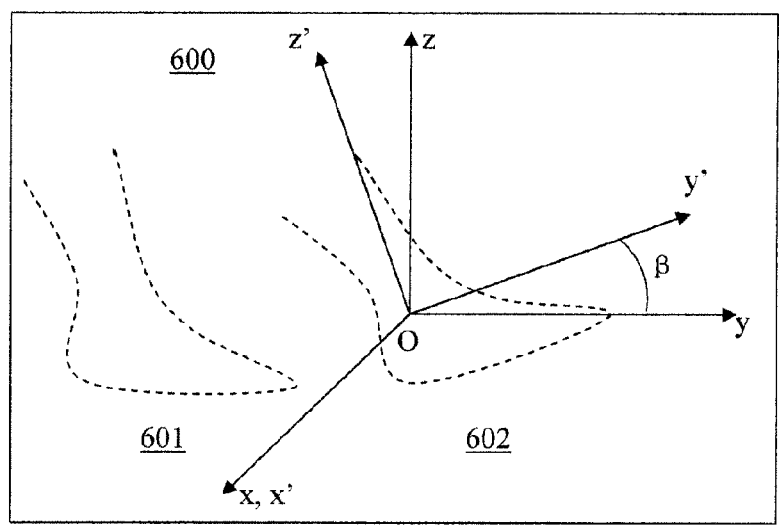
Figure 6B:
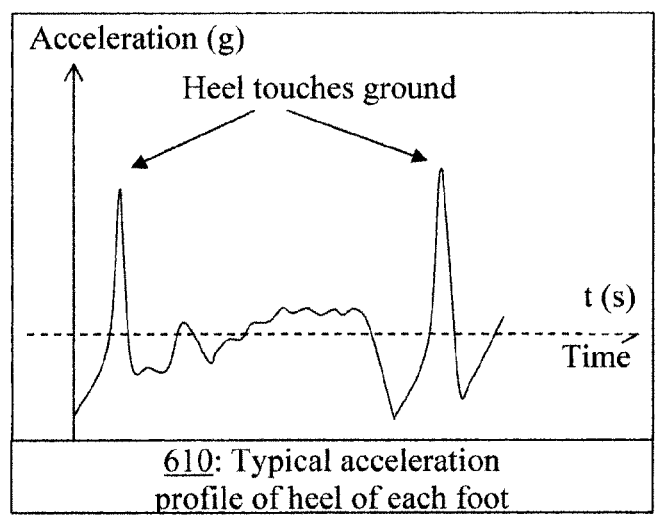

Referring to chart 600 in FIG. 6A, a sensor having 3-dimensional accelerometer mounted on a foot moving between positions 601 and 602 provides acceleration in the x', y', and z' directions. Knowing the pitch angle β(t) from the gyroscope, the accelerations $\alpha_x(t)$, $\alpha_y(t)$, $\alpha_z(t)$, can be obtained by coordinate transformation. For example, the pitch angle itself can be determined by integrating the angular velocity output from the gyroscope as described in equation 1.

$$\beta(t) = \int_0^t \dot{\beta}(\tau) d\tau \qquad \text{(Eq. 1)}$$

In situations where the wearer of the inertial sensors walks on an inclined surface, additional terms are included in the calculation of the pitch angle β(t).

The variable $\alpha_{x-y}$, is the resulting acceleration in the x-y plane, i.e., the ground surface, and may be obtained according to equation 2.

$$\alpha_{x-y}(t) = \sqrt{\alpha_y^2(t) + \alpha_x^2(t)} \qquad \text{(Eq. 2)}$$

If it is assumed that the initial velocity is zero, i.e., the person is starting from a fixed stance, the resultant velocity in the x-y plane ($v_{x-y}$) is obtained from equation 3.

$$v_{x-y}(t) = \int_0^t \alpha_{x-y}(\tau) d\tau \qquad \text{(Eq. 3)}$$

Continuing with FIG. 6A, the distance ($d_{x-y}$) of an advance made in the x–y plane, also defined to be the "step length," may be determined by equation 4.

$$d_{x-y}(t) = \int_0^t v_{x-y}(\tau)\,d\tau \qquad \text{(Eq. 4)}$$

Using equations 1-4, the vertical height reached during the swing phase of the foot between positions 601 and 602 may be determined by twice integrating the acceleration, $\alpha_z(t)$. The time history of the acceleration during the stance and swing phases, and the step length of both the left and right foot may be used to determine the left and right step lengths.

In this way, the sensor 530 may be sufficiently robust to accommodate different cases, while clearly differentiating the stance and swing phase of the gait cycle. Furthermore, several different known techniques may be used to integrate acceleration and velocity with respect to time, and any specific scheme may be selected to minimize error. Likewise, a particular sampling rate of analog to digital conversion may be selected as needed to achieve desired performance criteria.

Figure 7:
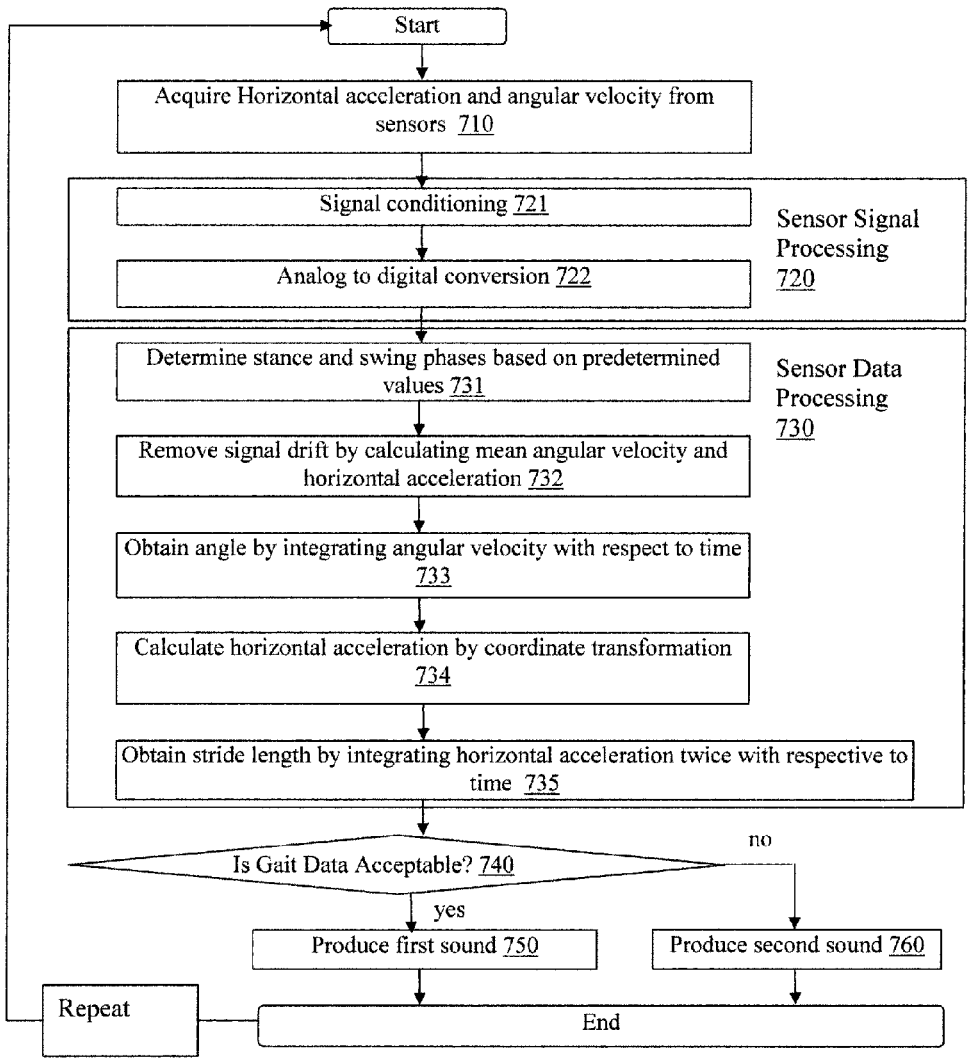
FIG. 7 depicts a dynamic audio cuing method in accordance with an embodiment of the present application.
Figure 8:
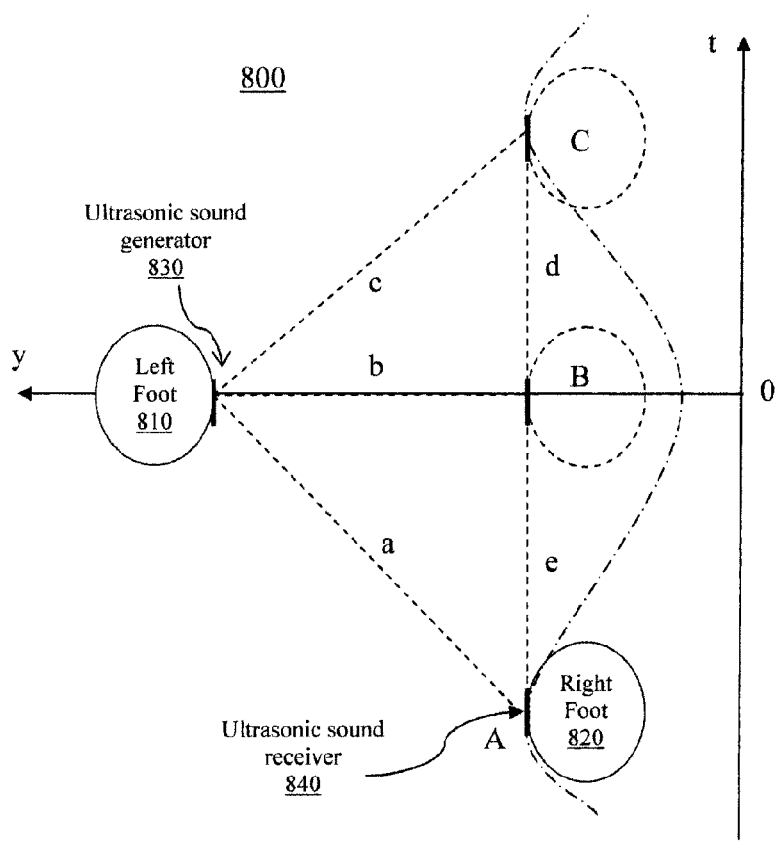
FIG. 8 depicts an ultrasonic sound sensor in accordance with an embodiment of the present application.

Referring now the FIG. 7, a dynamic audio cuing method 700 is presented. In step 710, horizontal acceleration and angular velocity data is acquired from the sensors, as described above. A signal forwarding this sensor data is processed in step 720. For example, the sensor signal may be conditioned to remove abnormalities in step 721 and sampled in step 722 to perform an analog to digital conversion.

The digital sensor data may then be processed in step 730. For example, as described above, stance and swing phases are determined in step 731 based on predetermined values. Signal drift may be removed in step 732 by calculating mean angular velocity and horizontal acceleration. The pitch angle of the gait may be obtained by integrating angular velocity with respect to time in step 733. Horizontal acceleration may then be calculated in step 734 by coordinate transformation. The step length for the gait cycle may then be obtained by integrating horizontal acceleration twice with respective to time in step 735.

The acquired gait data is analyzed in step 740 in comparison to an ideal gait. As described above, this ideal gait is typically defined in view of the particular need of the observed person. The actual and ideal gait may be evaluated based on, for example, differences between the left and right legs, and whether these differences exceed a predefined criterion. If the gait data does not adequately conform to the ideal gait, an audio cue is provided to direct the user in step 760 to better achieve the desired gait parameters. The process 700 can then repeat with additional gait measurements.

Referring now to FIG. 8, an ultrasonic sensor configuration 800 for a left foot 810 and right foot 820 is depicted. In the depicted configuration 800, the left foot 810 includes an ultrasonic sound generator 830 and the right foot 820 includes an ultrasonic sound receiver 840. It is noted that the ultrasonic sound generator and receiver are depicted as being fastened to opposite feet. The ultrasonic sound generator and receiver are not restricted as depicted (i.e., the ultrasonic sound generator can be on the right root with the ultrasonic sound receiver on the left foot, or vice versa). The ultrasonic sound generator 830 produces an ultrasonic sound signal that is detected by the ultrasonic sound receiver 840 as the right foot moves from starting point A to positions B and C. The ultrasound receiver 840 uses an ultrasonic sound signal from the ultrasound generator 830 to measures the distances directly, and specifically to measure distances a, b, and c. Using right-triangles, the distance d and e can also be obtained from a, b, and c. Where the observed person does not move in a straight path, right triangles are not formed, but the distances d and e can be still found by manually measuring distance b for particular user. Thus, the dynamic audio cuing method 700 could be adapted for use with the ultrasonic sound sensors in step 730, according to the functioning of the specific sensors.

Figure 9:
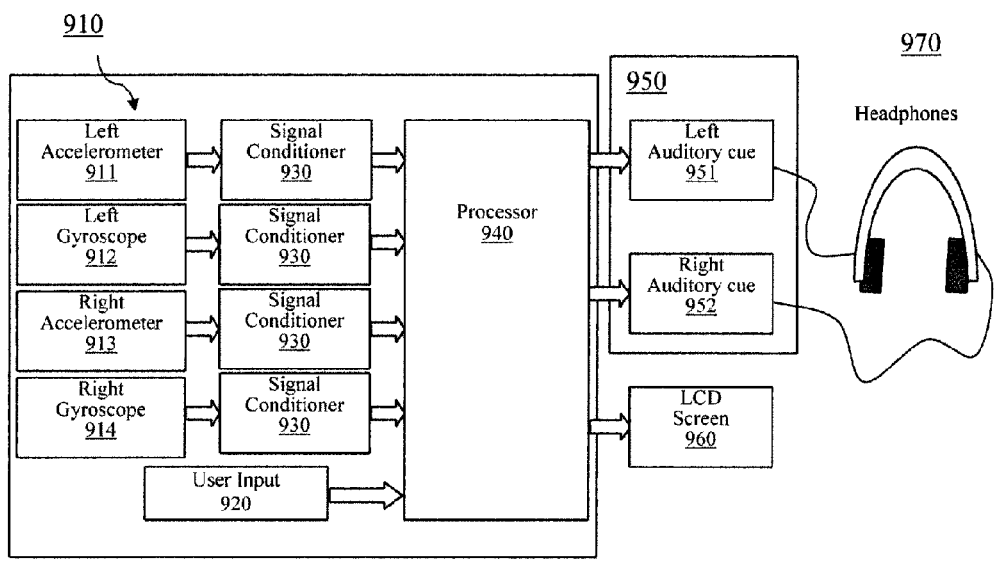
FIG. 9 depicts an audio cuing gait improvement device in accordance with an embodiment of the present application.

Referring now to FIG. 9, an audio cuing gait improvement device 900 is depicted. The device 900 includes a gait sensor 910 that has a left accelerometer 911, a left gyroscope 912, a right accelerometer 913, and a right gyroscope 912. The components of the sensor 910 are connected to a processor 940, such as a microcontroller, via a signal conditioner 930 that typically includes amplifiers and A/D converters. User input 920, such as a keypad and LCD screen allows the user to give commands to and read the messages from the device 900. A rhythmic auditory cue 950, optionally as separate left and right audio cues 951 and 952, can be delivered from a programmable IC chip (not depicted) integrated with the processor 940 or from a digital output port of the processor 940. The generated rhythmic auditory cues 950 can be given via headphones 970. The processor 940 may generate individualized rhythmic auditory cues 951, 952 with desired pitch and amplitude for each ear. Alternatively, a display screen 960 may visually display the gait cues.

As described above, the processor 940 may receive optimal gait parameters, such as step length and step time for given gait speed. These parameters may be customized for a given patient and are typically determined by a therapist or coach. The processor 940 may use equations for speed change based on normative data normalized for leg length. The rhythmic auditory cue rate can be set by the patient or therapist so that the sensor data can give feedback regarding whether the gait improvement goals are being met. Alternatively, when set in automatic control, the data from the sensor 910 representing the leg motions in the gait cycle may dictate the rhythmic auditory cue rate to which the patient can attempt to adhere.

Figure 10:
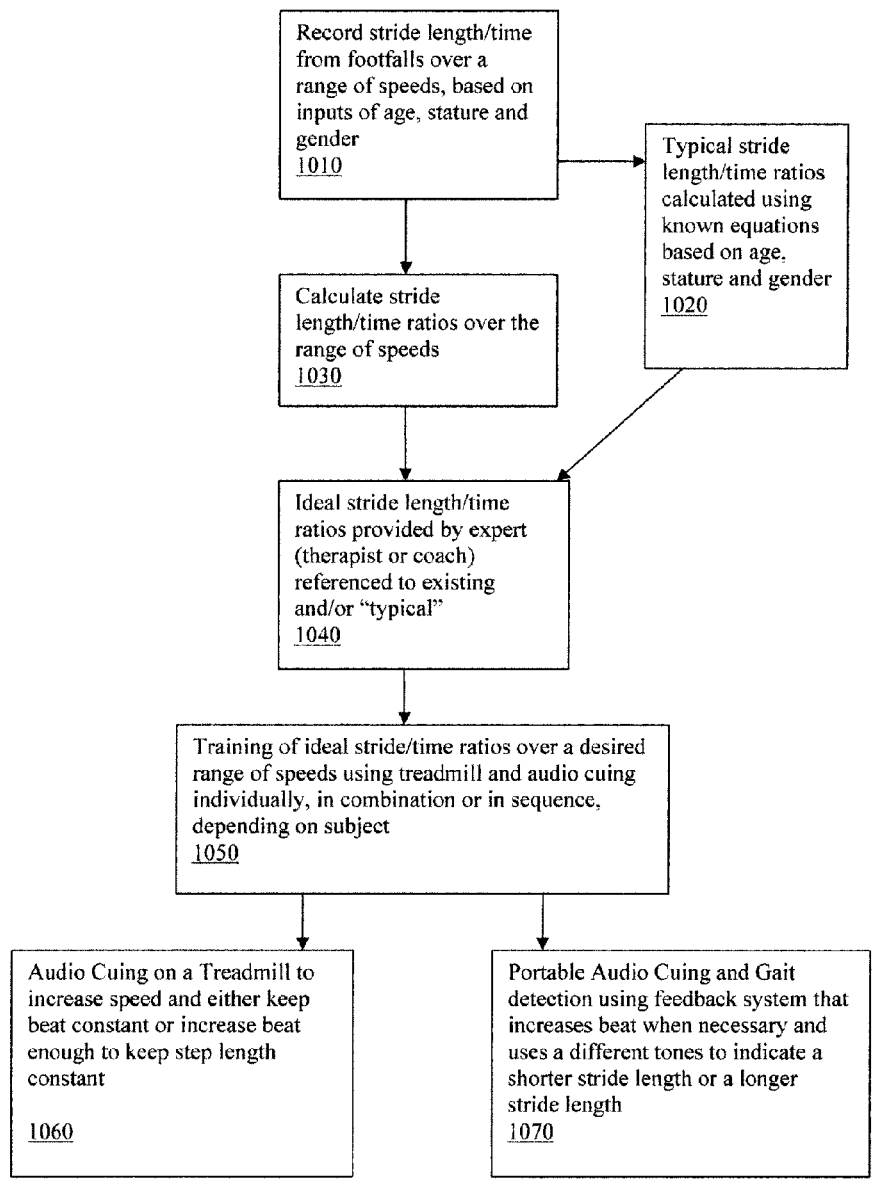
FIG. 10 depicts an audio cuing gait improvement method in accordance with an embodiment of the present application.

Referring now to FIG. 10, an audio cuing gait improvement method 1000 is depicted. In step 1010, step length/rate from footfalls are recorded over a range of speeds, based on inputs of age, stature and gender. Typical step length/rate ratios may be calculated using known equations based on age, stature and gender in step 1020. The step length/rate ratios may be calculated over a range of speeds in step 1030. In step 1040, an ideal step length/rate ratios is received from an expert (therapist or coach) and may be referenced to existing gait parameters data from step 1010 and/or typical gait parameters data from step 1020. In step 1050, various techniques disclosed in the present application may be used to train the user in the ideal stride length/time ratios over a desired range of speeds using treadmill and audio cuing individually, in combination or in sequence, depending on the user. For example, in step 1060, a user on a treadmill may receive audio cuing during an increase in speed by increasing treadmill speed. During the increase in treadmill speed in step 1060, the audio cues may be provided at a constant rate to encourage a larger step length to step rate ratio, or the rate of the audio cues may be increased sufficiently to maintain a constant step length, thereby increasing the step rate to step length ratio. Alternatively, portable audio cuing, as described above, may be used in step 1070 with a gait detection and feedback system that increases the rate of audio cues when needed to maintain/change a step length to step rate ratio and optionally uses different tones to indicate to the user whether to make a shorter step length or a longer step length.

Accordingly, certain embodiments of the present invention allow user to change their step length/rate ratios by following rhythmic auditory cues to actively make corresponding changes in the spatial and temporal gait parameters.

For example, in one embodiment, the presently described methods and equipment may be used in the therapy for individuals after a stroke (for example by, ischemia and/or reperfusion, blunt trauma, etc.). Other indications include use in the therapy for individuals with gait abnormalities resulting from neurodegenerative diseases (including, for example, multiple sclerosis, Parkinson's disease, Alzheimer's disease, Huntington's disease, amyotrophic lateral sclerosis (ALS), and myasthenia gravis), orthopedic corrective treatments (including, for example, surgical correction following a fracture or an arthroplasty (joint replacement)), aging, other diseases or conditions that cause gait abnormalities, and in an individual wishing to improve athletic performance by, for example, increasing certain gait parameters. In stroke patients, it is often necessary to help the patient lengthen stride/step length versus the step rate. In particular, the patient often achieves the desirable therapeutic goal of maintaining a minimum speed by only increasing their step rate in a weakened limb because these patients are anxious about taking longer steps. However, by shortening the length of steps on one side, the patients may become less stable and often have significant limitations in attainable speed increases.

In another embodiment, the present invention provides a therapy option for patients with Parkinson's disease. These patients have diminished sense of touch and therefore cannot accurately detect contact with the ground. For these patients, the audio cues may provide an alternative sensory feedback to enable the patients to maintain sufficient mobility.

In another embodiment, the present invention provides a therapy option for individuals with muscle weakness due to aging or other causes. Providing audio cuing to help these patients encourage to increase their walking speed, either through increased step lengths or step rates, depending on the needs of the patient.

In another embodiment, the present invention may be used to improve athletic performance in healthy users. For example, running speed may be improved by increasing step rate through use of rhythmic auditory cueing. Similarly, running speed may be improved by increasing the step length by providing positive audio feedback for longer strides.

For example, in one study, a first pilot subject demonstrated the feasibility of entraining to the RAC to achieve possible gait speed gains. This first pilot subject was a 63 year-old female, four years post stroke, with left hemiparesis who undertook a ten minute treadmill training session during which she timed her footfalls to a beat at 104 bpm (treadmill speed=1.23 m/s) and 112 bpm (treadmill speed=1.30 m/s). From observation and self-report, the subject was able to easily match her footfalls to the beat. As summarized in Table 1, the Post-OverGround (OG) results tended to be slower than Pre-OG in both comfortable and fast speeds, but this may have been due to the subject adjusting to over ground walking after treadmill walking. Furthermore, the combination of Post-RAC+OG immediately increased the subject's speed beyond Pre-OG levels in the slower speed condition primarily via longer stride lengths. In the fast condition, RAC+OG training shifted the stride length and speed closer to Pre-OG values. These findings suggest that RAC may be a translational mechanism between the treadmill and OG walking since it seems to maintain or improve on the Pre-OG gait velocities. Furthermore, for this first pilot subject, there was a slight trend for moving the symmetry ratios closer to 1 after the treadmill training with RAC+OG (in comfortable speed trials) but subject is already fairly symmetrical.

TABLE 1

| Gait Variables | Comfortable Speed | | | Faster, Safe Speed | | |
|---|---|---|---|---|---|---|
| | Pre-OG | Post-OG | Post-RAC + OG | Pre-OG | Post-OG | Post-RAC + OG |
| Speed (m/sec) | 1.17 | 0.94 | 1.27 | 1.35 | 1.26 | 1.38 |
| Stride Length (m) | 1.37 | 1.33 | 1.48 | 1.50 | 1.42 | 1.51 |
| Cadence (bpm) | 102 | 85 | 104 | 109 | 106 | 110 |
| Symmetry Ratio Step Length | 1.06 | 1.06 | 1.02 | 1.01 | 1.04 | 1.01 |
| Symmetry Ratio Step Time | 1.17 | 1.16 | 1.12 | 1.11 | 1.10 | 1.14 |

A second pilot subject demonstrated the feasibility of manipulating the stride-length alone as the means to adapt to increased treadmill speed and also that post-training gains are retained with RAC but not without the RAC. The second pilot subject was a 65 year-old male, seven years post stroke, with right hemiparesis who undertook a 10 minute treadmill training session during which he timed his footfalls to a constant beat of 96 cadence (1st treadmill speed 0.90 m/s; 2nd treadmill speed 1.12 m/s). From observation and self-report, the subject was able to initially match footfalls to the beat and maintain this matching at a higher speed resulting in increased stride-lengths. In this way, a change in stride-length was induced without a change in cadence. A second set of matching at a faster cadence 108 was also undertaken (1st treadmill speed 1.12 m/s; 2nd treadmill speed 1.34 m/s) with similar results.

The results for the second pilot subject are summarized in Table 2. Referring to the Table 2, in Post-OG with the second pilot subject, the relationship between speed and stride length returns to normal immediately after training if there is no concurrent RAC. With RAC+OG, at the same cadence as experienced on the treadmill, there is a partial/complete return to the new induced relationships between the gait parameters.

Figure 11:
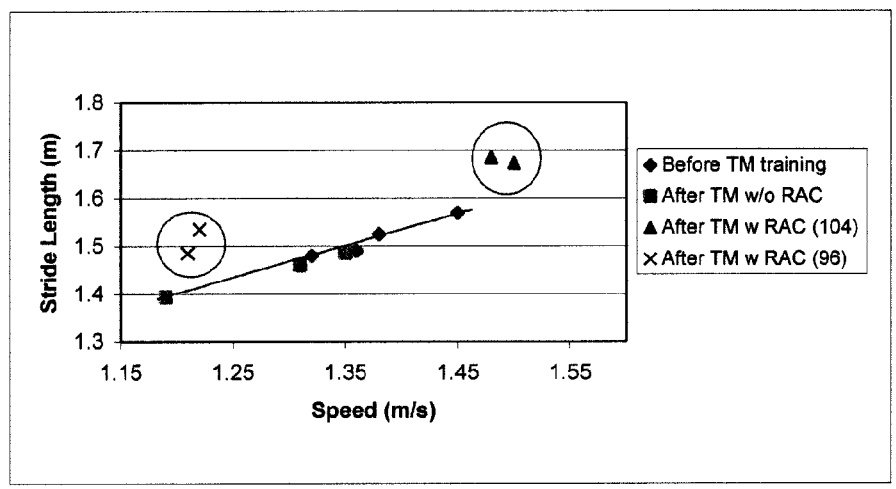
FIG. 11 depicts a chart representing results from a test subject receiving treatment in accordance with an embodiments of the present application.

This adjustment is depicted in FIG. 11 that includes a chart 1100 in which mean stride lengths and mean velocities were compared by plotting the pre and post-training gait. Notably, the pre-OG before TM trials and post-OG (w/o RAC) lie on a straight line. Continuing with FIG. 11, when RAC is reintroduced (RAC+OG), the stride lengths increase relative to the cadence suggesting a return to the relationship established on the treadmill (the circled data points). These results suggest that after a short training period, a new relationship between stride length and cadence can be established with combined treadmill and audio cueing. Although this relationship may be diminished immediately post training, this relationship can also be re-established by re-introducing RAC+OG. This again suggests that RAC+OG may provide a good translational mechanism between treadmill training in a clinical setting and the less constrained conditions of community-based walking.

TABLE 2

| Gait Variables | Comfortable Speed | | | Faster, Safe Speed | | |
|---|---|---|---|---|---|---|
| | Pre-OG | Post-OG | Post-RAC + OG | Pre-OG | Post-OG | Post-RAC + OG |
| Speed m/sec | 1.14 | 1.19 | 1.48 | 1.32 | 1.31 | 1.50 |
| Stride Length m | 1.35 | 1.39 | 1.69 | 1.48 | 1.46 | 1.67 |
| Cadence | 102 | 106 | 106 | 108 | 108 | 108 |
| Symmetry Ratio Length | 1.03 | 0.87 | 1.04 | 1.04 | 1.00 | 1.03 |

TABLE 2-continued

|  | Comfortable Speed | | | Faster, Safe Speed | | |
| --- | --- | --- | --- | --- | --- | --- |
| Gait Variables | Pre-OG | Post-OG | Post-RAC + OG | Pre-OG | Post-OG | Post-RAC + OG |
| Symmetry Ratio Time | .98 | 1.04 | 1.04 | .98 | .95 | .98 |

A study with a third pilot subject with lower functional level demonstrates feasibility and immediate gains in speed through the techniques and equipment disclosed in the present application. Specifically, the third pilot subject was a 68 year-old male, thirteen years post stroke, with left hemiparesis and undertook two bouts of about five minutes. From observation and self-report, the subject was able to match his footfalls to the beat but did not reach his comfortable OG walking speed until the second bout. The results for the third pilot subject are summarized in Table 3. Specifically, it can be seen that OG walking speed improved after therapy both with and without a cane. Similar to other pilots there was no clear change in symmetry although again, re-introducing RAC improved symmetry. These results suggest that the techniques and equipment disclosed in the present application can be used on subjects who are low functioning

TABLE 3

|  | Pre-training self-pace | | Post-training self-pace | | |
| --- | --- | --- | --- | --- | --- |
|  |  |  |  |  | Post RAC + OG |
| Gait Variables | w/o cane | With cane | w/o cane | With cane | w/o cane |
| Speed m/sec | 0.47 | 0.48 | 0.54 | 0.61 | 0.53 |
| Stride Length m | 0.82 | 0.88 | 0.87 | 0.98 | 0.87 |
| Cadence | 71 | 64 | 75 | 75 | 74 |
| Symmetry Ratio Length | 0.90 | 0.80 | 0.78 | 0.86 | 0.87 |
| Symmetry Ratio Time | 1.50 | 1.48 | 1.63 | 1.49 | 1.59 |

A study involving a fourth pilot subject demonstrated an increase in gait speed through twelve sessions over seven weeks. Specifically, the a fourth pilot subject was a 52 year-old male, four years post stroke with right hemiparesis, who received a twice-per-week treatment in accordance with the above-described techniques and equipment. It was determined that slightly shortening the fourth subject's stride length produced a more symmetrical and comfortable gait and so speed increases were accompanied by cadence increases slightly greater than his natural pattern. Over time, treadmill speed increased from 0.69 to 1.24 m/s and duration on the treadmill from 16 minutes to 30 minutes. Comfortable OG speed went from 0.75 m/s before to 0.92 m/s after training. Furthermore, this fourth pilot subject responded positively to a therapist providing verbal cues regarding the movement of each of the subject's legs. Although these verbal cues may provoke an intrinsic attentional focus that does not work as well in non-disabled subjects, the use of a sonic tone and verbal cues produced a positive, immediate response for this subject. Likewise, a kinematic secondary analysis of each leg's segmental coordination may be used because an increase in speed without change in the within-limb segmental relationships may result in less likelihood of maintaining the speed gain than if the fundamental limb coordination pattern is also changed towards a more efficient and adaptable movement pattern.

Although various embodiments which incorporate the teachings of the present invention have been shown and described in detail herein, those skilled in the art can readily devise other embodiments without departing from the basic scope of the present invention. For example, although the prior disclosure focuses on changing attributes of a user's gait, similar techniques could be used for other activities, such as bicycling, dancing, or swimming.

What is claimed:

1. A method for the improvement of a gait parameter in a subject in need thereof comprising:
   determining, using a processor, attributes of ideal spatial and temporal gait parameters of the subject;
   measuring attributes of actual spatial and temporal gait parameters of the subject comprising step length and step rate of the subject;
   determining, using a processor, a rhythmic audio cue based upon a desired gait change in the subject considering the attributes of ideal gait parameters and the attributes of the actual gait parameters; and
   providing to the subject said rhythmic audio cue wherein said providing of said rhythmic audio cue causes the subject to improve a gait parameter.

2. The method of claim 1, wherein improvement of a gait parameter is an increase in step length, step rate, or both step length and step rate.

3. The method of claim 1, wherein the determining of attributes of ideal spatial and temporal gait parameters is based on the age, stature, and gender of the subject.

4. The method of claim 1, wherein the determining of attributes of ideal spatial and temporal gait parameters comprises calculating a step length and step rate ratio for the subject using a plurality of speeds.

5. The method of claim 1, wherein the rhythmic audio cue is provided to the user on a treadmill.

6. The method of claim 1, wherein the rhythmic audio cue comprises two cueing signals comprising a tone and a beat.

7. The method of claim 6, wherein the tone comprises a first intensity that indicates to the subject a need for no change in step length, a second intensity that indicates to the subject a need for a shorter step length and is distinguishable from the first intensity, and a third intensity that is distinguishable from the first and second intensities and indicates to the subject a need for a longer step length; and
   wherein the beat comprises a pace comprising a constant beat that indicates to the subject a need for no change in step length, an increased pace that indicates to the subject a need for a shorter step length, a decreased pace that indicates to the subject a need for a longer step length.

8. The method of claim 1, wherein the subject has or is suffering from a disease or condition affecting gait selected from the group consisting of multiple sclerosis, Parkinson's disease, Alzheimer's disease, Huntington's disease, amyotrophic lateral sclerosis (ALS), stroke, aging, traumatic brain injury, and Myasthenia gravis.

9. An apparatus for the improvement of a gait parameter in a subject in need thereof, the apparatus comprising:
   a processor configured to
   determine attributes of ideal spatial and temporal gait parameters of the subject;
   receive data from a sensor, wherein the sensor is configured to measure attributes of actual spatial and temporal gait parameters of the subject comprising step length and step rate of the subject;
   determine a rhythmic audio cue based on desired gait changes in the subject considering attributes of ideal spatial and temporal gait parameters of the subject and the received sensor data of attributes of actual spatial and temporal gait parameters; and forward data configured to produce the rhythmic audio cue based on a desired gait change for the subject.

10. The apparatus of claim 9, wherein the sensor is configured to measure a horizontal acceleration and an angular acceleration of the subject.

11. The apparatus of claim 9, wherein the sensor comprises an accelerometer and a gyroscope.

12. The apparatus of claim 9, wherein the apparatus is portable and configured to provide the rhythmic audio cue when the subject is moving over ground.

13. The apparatus of claim 9, wherein determination of attributes of ideal spatial and temporal gait parameters is based on the age, stature, and gender of the subject.

14. The apparatus of claim 9, wherein determination of attributes of ideal spatial and temporal gait parameters comprises calculating a step length and step rate ratio for the subject using a plurality of speeds.

15. The apparatus of claim 9, further comprising a treadmill.

16. The apparatus of claim 9 further comprising an audio output device, wherein the audio output device is configured to provide an audio signal that will cue the individual as to how to alter their step length/step rate ratio by keeping time to the beat and, if over ground, by adjusting step length according to the tone pitch.

17. The apparatus of claim 9 further comprising an input/output device configured to enable the processor to provide or receive data to or from the subject.

18. The apparatus of claim 9 further comprising a signal conditioner between the sensor and the processor.

19. The apparatus of claim 9, wherein the rhythmic audio cue comprises a left rhythmic audio cue associated with a movement of a left limb and a right rhythmic audio cue associated with a movement of a right limb.

20. The apparatus of claim 9, wherein the rhythmic audio cue comprises an indication that the measured gait data conforms to an ideal gait or an indication that the measured gait data does not conform to the ideal gait.

\* \* \* \* \*